(12) United States Patent
Weber et al.

(10) Patent No.: US 6,933,419 B2
(45) Date of Patent: Aug. 23, 2005

(54) PRODUCTION OF DIISOPROPYLBENZENE

(75) Inventors: William A. Weber, Burlington, NJ (US); Walter R. Cade, Pennsauken, NJ (US); Francis S. Bryan, Townsend, DE (US); Jose Guadalupe Santiesteban, Bethlehem, PA (US)

(73) Assignee: ExxonMobil Oil Corporation, Irving, TX (US)

( * ) Notice: Subject to any disclaimer, the term of this patent is extended or adjusted under 35 U.S.C. 154(b) by 0 days.

(21) Appl. No.: 09/844,051

(22) Filed: Apr. 27, 2001

(65) Prior Publication Data

US 2003/0028061 A1 Feb. 6, 2003

(51) Int. Cl.$^7$ .............................................. C07C 15/12
(52) U.S. Cl. ....................................................... 585/475
(58) Field of Search ................................. 585/475, 323

(56) References Cited

U.S. PATENT DOCUMENTS

| | | | |
|---|---|---|---|
| 2,868,854 A | 1/1959 | Lien et al. ................... | 260/668 |
| 3,308,069 A | 3/1967 | Wadlinger et al. ........... | 252/455 |
| 3,449,070 A | 6/1969 | McDaniel et al. ............. | 23/111 |
| 3,766,093 A | 10/1973 | Chu ........................... | 252/455 |
| 3,780,123 A | 12/1973 | Suggitt ....................... | 260/672 |
| 3,894,104 A | 7/1975 | Chang et al. ................ | 260/668 |
| 4,367,359 A | 1/1983 | Kaeding ...................... | 585/467 |
| 4,415,438 A | 11/1983 | Dean et al. .................. | 208/120 |
| 4,439,409 A | 3/1984 | Puppe et al. ................. | 423/328 |
| 4,822,943 A | 4/1989 | Burress ....................... | 585/467 |
| 4,826,667 A | 5/1989 | Zones et al. ................. | 423/277 |
| 4,954,325 A | 9/1990 | Rubin et al. ................. | 423/328 |
| 4,992,606 A | 2/1991 | Kushnerick et al. ......... | 585/467 |
| 5,198,595 A | 3/1993 | Lee et al. .................... | 585/467 |
| 5,236,575 A | 8/1993 | Bennett et al. ............... | 208/46 |
| 5,243,116 A | 9/1993 | Lee et al. .................... | 585/467 |
| 5,250,277 A | 10/1993 | Kresge et al. ............ | 423/329.1 |
| 5,329,059 A | 7/1994 | Marler ........................ | 585/475 |
| 5,362,697 A | 11/1994 | Fung et al. ................... | 502/71 |
| 6,049,018 A * | 4/2000 | Calabro et al. .............. | 585/446 |

FOREIGN PATENT DOCUMENTS

| | | |
|---|---|---|
| DE | 4115263 | 11/1992 |
| EP | 0149508 | 7/1985 |
| EP | 149508 * | 7/1985 |
| GB | 764338 | 12/1956 |
| GB | 1395114 | 5/1975 |

OTHER PUBLICATIONS

Database Caplus online!; Chemical Abstracts Service, Columbus, Ohio, Isakov, Ya. I. Et al "Catalytic conversion of aromatic hydrocarbons in the presence of syntheti zeolites under atmospheric pressure" Database accession no. 68:29340; XP002207048 abstract & NEFTEKHIMIYA (1967), 7(4), 561–8.

Tsai, T: "Cumene disproportionation over zeolite beta I. Comparison of catalytic performances and reaction mechanisms of zeolites" Appl. Cat., vol. 77, 1991, pp. 199–207, XP001093860 tables.

A.I. Biaglow: "A probe of Bronsted site acidity in zeolites: 13C chemical shift of acetone" Journal of Catalysis, vol. 148, 1994, pp. 779–786, XP002207047, p. 780; table 1.

\* cited by examiner

*Primary Examiner*—Thuan D Dang
(74) *Attorney, Agent, or Firm*—Darryl M. Tyus; Linda A. Kubena

(57) ABSTRACT

A process for the disproportionation of cumene is disclosed which comprises the step of contacting a feed containing cumene, under disproportionation conditions, with a catalyst comprising a molecular sieve, preferably TEA-mordenite. The contacting step disproportionates at least part of the cumene in the feed to provide a disproportionation effluent containing benzene and a mixture of diisopropylbenzene isomers. The effluent is then recovered and contains, prior to any separation step, less 1% of ortho-diisopropylbenzene by weight of the total diisopropylbenzene content of said effluent, less than 1 wt % of n-propylbenzene, less than 5 wt % of triisopropylbenzenes and less than 5 wt % of disproportionation products other than benzene and diisopropylbenzenes.

10 Claims, No Drawings

PRODUCTION OF DIISOPROPYLBENZENE

This invention is directed to a process for the production of diisopropylbenzene (DIPB) and in particular to the production of DIPB rich in the meta- and para-isomers.

BACKGROUND OF THE INVENTION

Meta- and para-DIPB are important intermediates in organic synthesis. Thus resorcinol and hydroquinone can be prepared by oxidizing meta- and para-DIPB, respectively, with air and then decomposing the resulting dihydroperoxide with acid. However, although para-DIPB can be separated from a mixture of DIPB isomers by super fractionation, the boiling points of ortho- and meta-DIPB are too close to allow effective separation of meta-DIPB by fractionation. Moreover, ortho-DIPB is not readily oxidized and hence builds up in the production loop, requiring removal as a purge and representing a yield loss. Thus, to be commercially viable, any process for producing DIPB and, in particular meta-DIPB, must minimize the production of the ortho-isomer.

Currently, meta-DIPB is manufactured commercially by alkylating cumene with propylene over a homogeneous $AlCl_3$ catalyst. The high activity of the $AlCl_3$ catalyst produces a mixture of DIPB isomers with near equilibrium ortho content. This is advantageous since at equilibrium in the liquid phase between 50 and 150° C. the ratio of meta:ortho DIPB is greater than 100 providing sufficient purity for efficient downstream conversion to resorcinol. Process operation between 50 and 150° C. also results in DIPB products containing less than 1000 ppm of co-boiling n-propylisopropylbenzene impurities. However, corrosion and the need to neutralize, separate and recycle the $AlCl_3$ catalyst, make it difficult to employ.

DIPB can also be produced by separation from the polyalkylated by-product of the alkylation of benzene with propylene to produce cumene. However, DIPB separated from the polyalkylated fraction of current commercial cumene plants is rich in the kinetically preferred para- and ortho-DIPB isomers, making this route of limited use in the synthesis of meta-DIPB, unless the ortho- and para-content is reduced by, for example, isomerization or transalkylation. Transalkylation and isomerization, however, can introduce contaminant n-propyl-isopropylbenzenes.

Accordingly, there is an outstanding need for a heterogeneous process for producing DIPB rich in the meta-isomer and substantially free of the ortho-isomer and n-propylisopropylbenzenes.

U.S. Pat. No. 4,992,606 discloses a process for preparing short chain ($C_1$–$C_5$) alkylaromatic compounds by alkylation of an aromatic compound, such as benzene and cumene, with a short chain alkylating agent, such as propylene, over the molecular sieve MCM-22. In addition, U.S. Pat. No. 4,962,257 discloses the use of MCM-22 in the disproportionation of toluene to xylenes.

U.S. Pat. No. 5,329,059 discloses a process for the disproportionation of an alkylaromatic compound, wherein the alkyl group has from 1 to about 6 carbon atoms, e.g., cumene, by contacting said compound with catalyst comprising an active form of synthetic porous crystalline MCM-49.

U.S. Pat. No. 4,822,943 discloses a process for the selective production of para-DIPB by reacting cumene and/or benzene with propylene over the molecular sieve ZSM-12.

U.S. Pat. No. 5,198,595 discloses a process for preparing alkylaromatic compounds by alkylation of an aromatic compound with an alkylating agent having two to eighteen carbon atoms, such as propylene, over mordenite which has been subjected to repeated calcination and acid treatment so as to have a silica/alumina molar ratio of at least 40:1.

U.S. Pat. No. 6,049,018 discloses the porous crystalline material MCM-68 and its use in the alkylation of aromatics with short chain ($C_2$–$C_6$) olefins (for example, the alkylation of benzene with ethylene or propylene to produce ethylbenzene or cumene respectively), the transalkylation of aromatics (for example, the transalkylation of polyethylbenzenes or polyisopropylbenzenes with benzene to produce ethylbenzene or cumene respectively), and the disproportionation of alkylaromatics (for example, the disproportionation of toluene to produce xylenes).

U.S. Pat. No. 3,780,123 discloses the catalytic disproportionation of alkylbenzenes, including cumene, by contacting the alkylbenzene and a sulfide compound with hydrogen mordenite containing a sulfided Group VIII metal. According to Table 1 of U.S. Pat. No. 3,780,123, when mordenite is used to disproportionate cumene in the presence of methyldisulfide as the sulfide compound, the process produces a mixture of DIPB isomers in which the meta:ortho isomer ratio is between 58 and 85 and the product contains 4.4–7.2 wt % n-propylbenzene and 4.4–5.2 wt % of unidentified impurities. As a co-boiler with cumene, n-propylbenzene is an undesirable impurity, particularly since, on disproportionation, it yields n-propylisopropylbenzenes which tend to co-boil with meta-DIPB.

It will, of course, be understood that the disproportionation of cumene to produce DIPB and benzene is the inverse of the transalkylation of DIPB with benzene to produce cumene.

According to the invention, it has now been found that the disproportionation of cumene over a wide range of molecular sieve catalysts is unexpectedly more selective towards the production of meta-DIPB and less selective towards the production of ortho-DIPB than the alkylation of cumene with propylene over the same catalysts. Moreover, such molecular sieve catalysts produce relatively low concentrations of undesirable by-products, such as n-propylbenzene and triisopropylbenzenes. In particular, and contrary to the teaching in U.S. Pat. No. 3,780,123, it has been found that mordenite (in the absence of sulfided hydrogenation metal) can disproportionate cumene to produce DIPB in which the meta:ortho ratio is in excess of 500 and the by-product production is less than 1–2% by weight.

SUMMARY OF THE INVENTION

In one aspect, the invention resides in a process for the selective production of meta-diisopropylbenzene and para-diisopropylbenzene, said process comprising the steps of contacting cumene under disproportionation conditions with a catalyst comprising a molecular sieve to produce a disproportionation effluent containing benzene and a mixture of diisopropylbenzene isomers, and then recovering said effluent, wherein said effluent, prior to any separation step, contains less than 1% of ortho-diisopropylbenzene by weight of the total diisopropylbenzene content of said effluent, less than 1 wt % of n-propylbenzene, less than 5 wt % of triisopropylbenzenes and less than 5 wt % of disproportionation products other than benzene and diisopropylbenzenes.

Preferably, said effluent, prior to any separation step, has a meta-diisopropylbenzene to ortho-diisopropylbenzene ratio in excess of 50 and more preferably in excess of 100.

In a farther aspect, the invention resides in a process for the selective production of meta-diisopropylbenzene and para-diisopropylbenzene, said process comprising the step of contacting a feed containing cumene under disproportionation conditions with a catalyst comprising a molecular sieve having pores with a minimum cross-sectional dimension of at least 6 Angstrom to produce a disproportionation effluent containing benzene and a mixture of diisopropylbenzene isomers, wherein the feed is substantially free of benzene and the catalyst is substantially free of sulfided hydrogenation metal.

Preferably, said molecular sieve has pores with cross-sectional dimensions of between 6 and 7 Angstrom.

Preferably, said molecular sieve is selected from the group consisting of mordenite, zeolite beta, zeolite Y, and MCM-68. Most preferably, the molecular sieve is mordenite.

Preferably, said disproportionation conditions include a temperature of about 100 to about 300° C., a pressure of about 20 to about 5000 psig, a WHSV of about 0.01 to about 100 and a hydrogen to hydrocarbon molar ratio of 0 (no hydrogen added) to about 5.

More preferably, said disproportionation conditions include a temperature of about 140 to about 220° C., a pressure of about 20 to about 500 psig, a WYSV of about 0.1 to about 10 and a hydrogen to hydrocarbon molar ratio of 0 to about 5.

Preferably, said process comprises the initial steps of alkylating benzene with propylene to produce an alkylation effluent comprising cumene and then using at least part of said alkylation effluent as the feed to said contacting step.

Preferably, at least part of the benzene produced by said contacting step is recycled to the alkylating step.

DETAILED DESCRIPTION OF THE INVENTION

The present invention provides a process for producing a mixture of high purity diisopropylbenzene (DIPB) isomers near their equilibrium distribution at 180° C. of 65 wt % meta, 34.4 wt % para, and 0.6 wt % ortho by contacting a feed containing cumene, under disproportionation conditions, with a catalyst comprising a molecular sieve. The contacting step disproportionates at least part of said cumene to produce an effluent comprising benzene and a mixture of DIPB isomers. Prior to any separation step, the effluent contains less than 1% of ortho-DIPB by weight of the total DIPB content of said effluent, less than 1 wt % of n-propylbenzene, less than 5 wt % of triisopropylbenzenes (TIPB) and less than 5 wt % of disproportionation products other than benzene and DIPB. With the preferred catalyst, mordenite, for the first time DIPB's are shown to be produced with ortho-DIPB below its equilibrium value at 180° C. and the meta-isomer near its equilibrium value. Preferably, the weight ratio of meta-DIPB:ortho-DIPB in the as-produced effluent is greater than 50, more preferably greater than 100 and most preferably substantially exceeds equilibrium by being greater than 1000.

The molecular sieve used as the catalyst in the process of the invention has pores with a minimum cross-sectional dimension of at least 6 Angstrom and more preferably has pores with cross-sectional dimensions of between 6 and 7 Angstrom. Suitable molecular sieves have pores defined by channels formed by 12-membered rings of tetrahedrally coordinated atoms intersecting with channels formed by (a) 8-membered rings of tetrahedrally coordinated atoms or (b) 10-membered rings of tetrahedrally coordinated atoms or (c) 12-membered rings of tetrahedrally coordinated atoms.

An example of molecular sieve (a) is mordenite which, although naturally-occurring, is preferably used in a synthetic form, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104, the entire contents of which patents are incorporated herein by reference. An example of molecular sieve (b) is MCM-68, the composition, synthesis and use of which in toluene disproportionation is disclosed in U.S. Pat. No. 6,049,018, the entire contents of which are incorporated herein by reference. Examples of molecular sieve (c) are zeolite beta and zeolite Y, such as Ultrastable Y (USY) and rare earth exchanged Y (REY). Zeolite beta is disclosed in U.S. Pat. No. 3,308,069, USY is disclosed in U.S. Pat. No. 3,449,070 and REY is disclosed in U.S. Pat. No. 4,415,438, the entire contents of which patents are incorporated herein by reference.

Preferably, the molecular sieve used in the process of the invention is TEA-mordenite and especially TEA-mordenite having an average crystal size of less than 0.5 micron and a silica alumina molar ratio of about 25 to about 50. The required small crystal TEA-mordenite can be produced by crystallization from a synthesis mixture having a molar composition within the following ranges:

|  | | Useful | Preferred |
|---|---|---|---|
| R/R + Na$^+$ | = | >0.4 | 0.45–0.7 |
| OH$^-$/SiO$_2$ | = | <0.22 | 0.05–0.2 |
| Si/Al$_2$ | = | >30–90 | 35–50 |
| H$_2$O/OH | = | 50–70 | 50–60 |

The crystallization is conducted at a temperature of 90 to 200° C., for a time of 6 to 180 hours.

The molecular sieve used in the process of the invention does not contain the sulfided hydrogenation metal disclosed in U.S. Pat. No. 3,780,123 and is not subjected to acid-leaching as, for example, disclosed in U.S. Pat. No. 5,243,116.

As in the case of many catalysts, it may be desirable to incorporate the molecular sieve component of the catalyst of the invention with another material resistant to the temperatures and other conditions employed in cumene disproportionation. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material which is active tends to change the conversion and/or selectivity of the catalyst in the disproportionation process. Inactive materials suitably serve as diluents to control the amount of conversion in the process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the active molecular sieve component include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, such as silica, zirconia, titania, magnesia, beryllia, alumina, and mixtures thereof.

In addition to the foregoing materials, the active molecular sieve component can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of active molecular sieve component and inorganic oxide matrix vary widely, with the crystal content ranging from about 1 to about 90 percent by weight and more usually, particularly when the composite is prepared in the form of beads, in the range of about 2 to about 80 weight percent of the composite.

The conditions used in the process of the invention should be such as to effect significant disproportionation of the cumene in the feed while minimizing the production of by-products, particularly n-propylisopropylbenzenes, triisopropylbenzenes and other heavy materials. Suitable conditions include a temperature of about 100 to about 300° C., a pressure of about 20 to about 5000 psig, a WHSV of about 0.01 to about 100 and a hydrogen to hydrocarbon molar ratio of 0 (no hydrogen added) to about 50. More preferably, the conditions include a temperature of about 140 to about 220° C., a pressure of about 20 to about 500 psig and WHSV of about 0.1 to about 10 and a hydrogen to hydrocarbon molar ratio of about 0 to about 5.

The feed to the process of the invention can contain 75 to 100% by weight of cumene and preferably at least about 90% by weight of cumene. Preferably, the feed is substantially free of benzene so as to minimize unwanted side reactions, such as transalkylation of benzene with the DIPB product. The feed is also free of added sulfide, such as the methyldisulfide disclosed in U.S. Pat. No. 3,780,123. In particular, the feed can be cumene purchased on the open market or, more preferably, is the direct product of a commercial cumene plant in which benzene is alkylated with propylene over a suitable catalyst. One particularly preferred embodiment uses the product or a slip-stream of a commercial cumene plant in which the benzene alkylation step is conducted in the presence of an alkylation catalyst comprising a molecular sieve catalyst selected from zeolite beta, MCM-22, PSH-3, SSZ-25, MCM-36, MCM-49 or MCM-56 to produce an alkylation effluent comprising cumene and polyisopropylbenzenes. The cumene is recovered from the alkylation effluent and the polyisopropylbenzenes are separated and fed to a transalkylation unit in which they are converted to additional cumene by transalkylation with benzene in the presence of transalkylation catalyst selected from zeolite beta, mordenite, MCM-22, PSH-3, SSZ-25, MCM-36, MCM-49 or MCM-56.

MCM-22 is described in U.S. Pat. No. 4,954,325, PSH-3 is described in U.S. Pat. No. 4,439,409, SSZ-25 is described in U.S. Pat. No. 4,826,667, MCM-36 is described in U.S. Pat. No. 5,250,277, MCM-49 is described in U.S. Pat. No. 5,236,575 and MCM-56 is described in U.S. Pat. No. 5,362,697.

The products of the disproportionation process of the invention are benzene and a mixture of DIPB isomers, in which the weight ratio of meta-DIPB:ortho-DIPB is typically greater than 50, preferably greater than 100 and more preferably greater than 500. Impurity levels in the product are very low, with n-propylbenzene content being less than 1 wt % and preferably less than 0.5 wt %, the TIPB content being less than 5 wt % and preferably less than 1 wt %, and the total content of disproportionation products other than benzene and DIPB being less than 5 wt % and preferably less than 2 wt %.

The benzene coproduced with the DIPB in the process of the invention is relatively free of co-boiling impurities and hence it can be separated, for example, by distillation, and sold as extraction grade benzene. Alternatively, where the cumene feed is produced by an initial benzene alkylation step, the benzene produced in the process of the invention can be separated and recycled to the alkylation reactor.

The DIPB product of the process of the invention typically contains about 40–70% by weight of the meta isomer and 30–60% by weight of the para-isomer. The individual DIPB isomers can be separated by any convenient means, such as by super-fractionation. If, however, it is required to increase the yield on one of these isomers, say the meta-isomer, it is possible to recycle some or all of the other isomer, say the para-isomer, to the disproportionation reactor, where the para-DIPB will be isomerized to produce the meta-isomer with little or no co-production of the ortho-isomer.

The invention will now be more particularly described with reference to the following Examples. In the Examples, the cumene employed was chemical grade cumene which had been purified by percolation over activated alumina.

EXAMPLE 1

COMPARATIVE

Alkylation of Cumene Over TEA-Mordenite 2 g of a TEA-mordenite catalyst (1/16" extrudates with 35 wt % alumina binder) were used to alkylate cumene with commercial grade propylene. The TEA-mordenite used in the catalyst had a silica/alumina molar ratio of 37 and was produced from a synthesis mixture which comprised water, precipitated silica, aluminum sulfate solution, sodium hydroxide and tetraethylammonium bromide and which had the following molar composition (based alumina=1):

| silica | = | 39.7 |
|---|---|---|
| $Na_2O$ | = | 7.3 |
| $SO_4^-$ | = | 2.9 |
| TEA | = | 12.3 |
| water | = | 370 |

The synthesis mixture was crystallized at 149° C. (300° F.) with stirring at 90 RPM for 40–44 hrs. The resultant TEA-mordenite was isolated by filtration, washed and dried and found to have a crystal size by scanning electron microscopy of <0.5 micron.

The catalyst was diluted with about 2 g of sand and charged to a down-flow 3/8" external diameter, stainless steel fixed bed reactor. The catalyst was dried at 125° C. and 1 atm pressure with 100 cc/min flowing $N_2$ for 2 hours. While retaining $N_2$ flow, the reactor pressure was set to 850 psig by a grove loader and the reactor temperature was adjusted to the desired temperature for the first set of alkylation conditions (160° C.). The feed, containing cumene and propylene in the molar ratio stated in Table 1, was introduced to the reactor at the WUSV stated in Table 1. After lining out for 24 hours, liquid products were collected in a cold-trap and analyzed off-line with a Hewlett-Packard 5890 Gas Chromatograph. The catalyst was tested at several conditions, with each condition being lined out for 24 hours before collecting a liquid product. The results are shown in Table 1.

TABLE 1

| Conditions | | | | |
|---|---|---|---|---|
| Temperature, C. | 140 | 160 | 180 | 200 |
| Pressure, psig | 850 | 850 | 850 | 850 |
| Ring/Alkylate (molar) | 4 | 4 | 4 | 4 |
| WHSV | 2 | 2 | 2 | 2 |
| Reactor Effluent | | | | |
| C5− | 0.99% | 1.76% | 1.36% | 0.61% |
| Benzene | 0.00% | 0.00% | 0.00% | 0.00% |
| Toluene | 0.00% | 0.00% | 0.07% | 0.00% |
| EB | 0.01% | 0.00% | 0.00% | 0.00% |
| Cumene | 86.94% | 82.24% | 78.00% | 77.28% |
| DIPB | 11.66% | 15.63% | 19.97% | 21.14% |
| COMDIPB | 0.01% | 0.00% | 0.00% | 0.00% |
| C8–C10 Aromatics | 0.08% | 0.03% | 0.04% | 0.05% |
| TIPB | 0.06% | 0.07% | 0.15% | 0.21% |
| C10+ Aromatics | 0.25% | 0.25% | 0.40% | 0.70% |
| Cumene Conversion Selectivity | 5.45% | 10.56% | 15.17% | 15.95% |
| MDIPB | 29.08% | 27.95% | 28.72% | 29.23% |
| ODIPB | 0.96% | 1.27% | 1.61% | 1.90% |
| PDIPB | 69.96% | 70.78% | 69.68% | 68.87% |
| PDIPB Purity | 96.42% | 97.22% | 96.19% | 94.11% |
| MDIPB Purity | 96.59% | 95.58% | 94.65% | 93.88% |
| MDIPB:ODIPB Ratio | 30.2 | 22.0 | 17.9 | 15.4 |

EXAMPLE 2

Disproportionation of Cumene Over TEA-Mordenite

The catalyst and apparatus of Example 1 were used to effect disproportionation of cumene under the conditions summarized in Table 2. As before, the catalyst was tested at several conditions, with each condition being lined out for 24 hours before liquid products were collected in a cold-trap and analyzed off-line with an HP 5890 GC. The results are shown in Table 2.

TABLE 2

| Conditions | | | | | | | | |
|---|---|---|---|---|---|---|---|---|
| WHSV | 2 | 2 | 2 | 2 | 2 | 2 | 2 | 2 |
| Temperature, C. | 170 | 180 | 190 | 200 | 210 | 220 | 230 | 240 |
| Pressure, psig | 850 | 850 | 850 | 850 | 850 | 850 | 850 | 850 |
| Reactor Effluent (wt %) | | | | | | | | |
| DIPB | 24.66% | 27.35% | 26.56% | 24.05% | 25.29% | 25.48% | 23.33% | 23.69% |
| COMDIPB | 0.00% | 0.00% | 0.00% | 0.00% | 0.00% | 0.00% | 0.00% | 0.00% |
| Cumene | 58.93% | 59.57% | 60.65% | 64.15% | 62.27% | 61.27% | 64.99% | 64.35% |
| Benzene | 12.88% | 12.69% | 12.33% | 11.30% | 11.85% | 12.07% | 10.90% | 11.09% |
| TIPB | 0.01% | 0.00% | 0.00% | 0.00% | 0.00% | 0.02% | 0.00% | 0.02% |
| C10+ | 0.16% | 0.19% | 0.28% | 0.34% | 0.42% | 0.60% | 0.60% | 0.65% |
| Toluene | 1.66% | 0.08% | 0.07% | 0.06% | 0.05% | 0.23% | 0.03% | 0.03% |
| EB | 0.01% | 0.01% | 0.01% | 0.01% | 0.01% | 0.01% | 0.01% | 0.02% |
| C5− | 0.00% | 0.01% | 0.01% | 0.01% | 0.02% | 0.02% | 0.01% | 0.02% |
| Selectivities | | | | | | | | |
| MDIPB | 64.93% | 64.87% | 64.79% | 64.55% | 64.71% | 64.38% | 63.20% | 63.25% |
| ODIPB | 0.03% | 0.03% | 0.04% | 0.03% | 0.04% | 0.06% | 0.06% | 0.06% |
| PDIPB | 35.04% | 35.11% | 35.17% | 35.43% | 35.25% | 35.56% | 36.74% | 36.68% |

TABLE 2-continued

| | | | | | | | | |
|---|---|---|---|---|---|---|---|---|
| Purity MDIPB | 99.92% | 99.96% | 99.95% | 99.96% | 99.93% | 99.90% | 99.91% | 99.90% |
| Ratio MDIPB:ODIPB | 2117.9 | 2313.2 | 1828.6 | 2330.5 | 1469.3 | 1041.7 | 1142.9 | 981.2 |
| Cumene Conversion | 41.07% | 40.43% | 39.35% | 35.85% | 37.73% | 38.73% | 35.01% | 35.65% |

From Examples 1 and 2, it will be seen that cumene disproportionation over TEA-mordenite is considerably more selective to meta-DIPB and less selective to ortho-DIPB than cumene propylation. Thus meta-DIPB to ortho-DIPB ratios from about 1000 to in excess of 2000 and meta-DIPB to para-DIPB ratios of 1.7 to 1.8 were obtained by disproportionation over a temperature range of 170 to 240° C. and cumene conversions of 35 to 40%, whereas alkylation gave meta-DIPB to ortho-DIPB ratios of only 15 to 30 and meta to para of less than 0.5 over a temperature range of 140 to 200° C. and cumene conversions of 5 to 16%. In addition, it will be seen from Table 2 that cumene disproportionation gave a product which was essentially free of n-propylbenzene and meta-DIPB co-boilers (COMDIPB in the Tables) and in which the triisopropylbenzene (TIPB) was less than 0.2 wt % and the total by-product content was less than 2 wt %.

EXAMPLE 3

Disproportionation of Cumene Over TEA-Mordenite

The process of Example 2 was repeated but with the temperature and pressure being held at 170° C. and 300 psig respectively and the products being analyzed at various times over a run of 22 days. The results are summarized in Table 3.

TABLE 3

| Days on stream | 1 | 2 | 4 | 10 | 14 | 18 | 22 |
|---|---|---|---|---|---|---|---|
| WHSV | 2 | 2 | 2 | 2 | 2 | 2 | 2 |
| H2/HC molar | 0 | 0 | 0 | 0 | 0 | 0 | 0 |
| Reactor Effluent (wt %) | | | | | | | |
| C5- | 0.09% | 10.06% | 0.01% | 0.01% | 0.01% | 0.01% | 0.01% |
| C6/C7 | 0.03% | 0.00% | 0.00% | 0.00% | 0.00% | 0.00% | 0.00% |
| Benzene | 10.70% | 0.04% | 10.50% | 10.49% | 10.58% | 11.18% | 9.90% |
| Toluene | 0.02% | 0.00% | 0.00% | 0.00% | 0.00% | 0.00% | 0.00% |
| EB | 0.20% | 0.00% | 0.00% | 0.00% | 0.00% | 0.00% | 0.00% |
| Cumene | 63.29% | 69.00% | 67.99% | 66.67% | 66.62% | 65.25% | 69.08% |
| DIPB | 24.14% | 20.76% | 21.34% | 22.67% | 22.64% | 23.4% | 20.86% |
| COMDIPB | 0.00% | 0.00% | 0.00% | 0.00% | 0.00% | 0.00% | 0.00% |
| C8–C10 Aromatics | 1.32% | 0.00% | 0.03% | 0.03% | 0.03% | 0.04% | 0.03% |
| TIPB | 0.00% | 0.00% | 0.00% | 0.00% | 0.00% | 0.00% | 0.00% |
| C10+ | 0.21% | 0.13% | 0.13% | 0.13% | 0.11% | 0.12% | 0.12% |
| Cumene conversion | 36.71% | 31.00% | 32.01% | 33.33% | 33.38% | 34.75% | 30.92% |
| Selectivities | | | | | | | |
| MDIPB | 64.87% | 64.35% | 64.50% | 64.54% | 64.58% | 64.64% | 64.33% |
| ODIPB | 0.06% | 0.06% | 0.05% | 0.05% | 0.05% | 0.05% | 0.05% |
| PDIPB | 35.07% | 35.59% | 35.45% | 35.41% | 35.37% | 35.30% | 35.62% |
| MDIPB:ODIPB Ratio | 1050 | 1162 | 1240 | 1210 | 1246 | 1197 | 1264 |

EXAMPLE 4

Disproportionation of Cumene Over TEA-Mordenite (H₂ Co-Feed)

The process of Example 3 was repeated again at a temperature of 170° C. and a pressure of 300 psig, but in this case with hydrogen being cofed with the cumene. The results are summarized in Table 4.

TABLE 4

| Days on stream | 1 | 2 | 4 | 10 | 14 | 18 | 22 |
|---|---|---|---|---|---|---|---|
| WHSV | 2 | 2 | 2 | 2 | 2 | 2 | 2 |
| H2/HC molar | 1 | 1 | 1 | 1 | 1 | 1 | 1 |
| Reactor Effluent (wt %) | | | | | | | |
| C5- | 0.02% | 0.00% | 0.00% | 0.00% | 0.00% | 0.00% | 0.00% |
| C6/C7 | 0.02% | 0.01% | 0.00% | 0.00% | 0.00% | 0.00% | 0.00% |
| Benzene | 12.78% | 13.79% | 14.04% | 13.53% | 13.29% | 13.78% | 13.27% |

TABLE 4-continued

| | | | | | | | |
|---|---|---|---|---|---|---|---|
| Toluene | 0.00% | 0.01% | 0.00% | 0.00% | 0.00% | 0.00% | 0.00% |
| EB | 0.00% | 0.01% | 0.00% | 0.00% | 0.00% | 0.00% | 0.00% |
| Cumene | 60.40% | 54.78% | 53.18% | 55.76% | 54.99% | 55.27% | 56.88% |
| DIPB | 26.49% | 31.12% | 32.49% | 30.47% | 31.47% | 30.70% | 29.61% |
| COMDIPB | 0.00% | 0.00% | 0.00% | 0.00% | 0.00% | 0.00% | 0.00% |
| C8–C10 Aromatics | 0.06% | 0.07% | 0.05% | 0.04% | 0.05% | 0.04% | 0.04% |
| TIPB | 0.01% | 0.01% | 0.01% | 0.00% | 0.01% | 0.01% | 0.00% |
| C10+ | 0.22% | 0.21% | 0.22% | 0.19% | 0.20% | 0.19% | 0.18% |
| Cumene conversion | 39.60% | 45.22% | 46.82% | 44.24% | 45.01% | 44.35% | 43.12% |
| Selectivities | | | | | | | |
| MDIPB | 64.94% | 65.30% | 65.35% | 65.29% | 65.22% | 65.27% | 65.20% |
| ODIPB | 0.09% | 0.08% | 0.08% | 0.07% | 0.07% | 0.07% | 0.06% |
| PDIPB | 34.97% | 34.62% | 34.56% | 34.64% | 34.71% | 34.66% | 34.73% |
| MDIPB:ODIPB Ratio | 718 | 839 | 771 | 890 | 920 | 896 | 1014 |

Comparing the results in Tables 3 and 4, it will be seen that the addition of the hydrogen cofeed significantly increased the cumene conversion with only marginal decrease in the meta:ortho DIPB level. In both cases, there was little or no evidence of catalyst aging over the 22 days on stream.

EXAMPLE 5

Disproportionation of Cumene Over Zeolite Beta

The procedure of Example 2 was repeated but with the catalyst being 2 g of zeolite beta (1/16" extrudates with 35 wt % alumina binder), again diluted with about 2 g of sand. The results are shown in Table 5.

TABLE 5

| Conditions | | | | | | | | | |
|---|---|---|---|---|---|---|---|---|---|
| WHSV | 2 | 2 | 2 | 2 | 2 | 2 | 2 | 2 | 2 |
| Pressure, psig | 850 | 850 | 850 | 850 | 850 | 850 | 850 | 850 | 850 |
| Temperature, C. | 160 | 170 | 180 | 190 | 200 | 210 | 220 | 230 | 240 |
| Reactor Effluent (wt %) | | | | | | | | | |
| DIPB | 1.77% | 23.89% | 28.60% | 31.42% | 31.65% | 31.26% | 29.47% | 28.74% | 25.00% |
| COMDIPB | 0.01% | 0.00% | 0.00% | 0.00% | 0.00% | 0.00% | 0.02% | 0.02% | 0.06% |
| Cumene | 96.59% | 65.36% | 56.82% | 53.18% | 50.73% | 49.72% | 49.03% | 47.98% | 47.21% |
| Benzene | 0.83% | 10.26% | 13.84% | 14.32% | 15.61% | 15.90% | 16.84% | 16.62% | 18.41% |
| TIPB | 0.01% | 0.03% | 0.07% | 0.13% | 0.27% | 0.40% | 0.63% | 0.98% | 1.10% |
| C10+ | 0.08% | 0.21% | 0.40% | 0.62% | 1.18% | 1.82% | 2.47% | 3.38% | 4.51% |
| Toluene | 0.00% | 0.13% | 0.10% | 0.08% | 0.07% | 0.06% | 0.13% | 0.07% | 0.09% |
| EB | 0.01% | 0.00% | 0.01% | 0.02% | 0.05% | 0.10% | 0.20% | 0.32% | 0.57% |
| C5- | 0.00% | 0.00% | 0.02% | 0.04% | 0.12% | 0.31% | 0.31% | 0.66% | 1.06% |
| Selectivities | | | | | | | | | |
| MDIPB | 56.90% | 64.45% | 64.96% | 65.08% | 65.20% | 65.23% | 65.33% | 65.34% | 65.35% |
| ODIPB | 0.61% | 0.44% | 0.49% | 0.56% | 0.59% | 0.64% | 0.69% | 0.72% | 0.81% |
| PDIPB | 42.49% | 35.10% | 34.54% | 34.36% | 34.21% | 34.13% | 33.98% | 33.93% | 33.84% |
| MDIPB:ODIPB Ratio | 94.0 | 145.3 | 131.5 | 117.3 | 109.7 | 101.2 | 94.9 | 90.4 | 80.5 |
| Cumene Conversion | 3.4% | 34.6% | 43.2% | 46.8% | 49.3% | 50.3% | 51.0% | 52.0% | 52.8% |

From the results in Table 5 it will be seen that at cumene conversions of 35–50%, zeolite beta gave a mixture of DIPB isomers in which the meta:ortho ratio varied from 100–145 and the yield of total by-products was <1 wt %.

EXAMPLE 6

COMPARATIVE

Alkylation of Cumene Over Zeolite Beta

The catalyst and reactor of Example 5 were used to alkylate a feed comprising a mixture of commercial grade benzene and propylene using the procedure of Example 1. The results are shown in Table 6.

TABLE 6

| Conditions | | | | |
|---|---|---|---|---|
| Temperature, C. | 140 | 160 | 180 | 200 |
| Ring/Alkylate molar | 4 | 4 | 4 | 4 |
| WHSV | 2 | 2 | 2 | 2 |
| Reactor Feed | | | | |
| Cumene | 91.95% | 91.95% | 91.95% | 91.95% |
| Propylene | 8.05% | 8.05% | 8.05% | 8.05% |

TABLE 6-continued

| Reactor Effluent | | | | |
|---|---|---|---|---|
| C5- | 0.56% | 0.41% | 0.49% | 0.58% |
| Benzene | 0.00% | 0.01% | 0.13% | 0.74% |
| Toluene | 0.00% | 0.00% | 0.00% | 0.00% |
| EB | 0.02% | 0.00% | 0.01% | 0.01% |
| Cumene | 75.80% | 76.55% | 73.97% | 74.08% |
| DIPB | 20.05% | 20.25% | 21.57% | 21.01% |

TABLE 6-continued

| | | | | |
|---|---|---|---|---|
| COMDIPB | 0.01% | 0.01% | 0.00% | 0.01% |
| C8–C10 Aromatics | 0.04% | 0.03% | 0.04% | 0.06% |
| TIPB | 0.85% | 0.82% | 0.97% | 0.76% |
| C10+ | 2.68% | 1.92% | 2.83% | 2.75% |
| Cumene Conversion | 17.57% | 16.75% | 19.56% | 19.43% |
| Selectivities | | | | |
| MDIPB | 39.80% | 39.80% | 39.80% | 44.42% |
| ODIPB | 6.99% | 6.99% | 6.54% | 5.35% |
| PDIPB | 53.21% | 53.21% | 53.66% | 50.22% |
| MDIPB:ODIPB Ratio | 5.7 | 5.7 | 6.1 | 8.3 |

It will be seen from Table 6 that preparation of DIPB by alkylation over zeolite beta produced a mixture of isomers in which the meta:ortho ratio was only 5–8 as compared with the values of 100–145 obtained by disproportionation. Total byproduct yields exceed 3 wt %.

EXAMPLE 7

Disproportionation of Cumene Over RE-Y

The process of Example 2 was repeated but with the catalyst being 2 g of RE-Y (crushed 1/8" extrudates with 35% alumina binder) diluted with about 2 g of sand. The results are shown in Table 7.

TABLE 7

| Conditions | | | | |
|---|---|---|---|---|
| Temperature, C. | 160 | 180 | 200 | 220 |
| Pressure, psig | 850 | 850 | 850 | 850 |
| WHSV | 2 | 2 | 2 | 2 |
| Reactor Effluent | | | | |
| C5– | 0.00% | 0.00% | 0.09% | 0.45% |
| Benzene | 1.15% | 3.33% | 14.15% | 16.98% |
| Toluene | 0.00% | 0.00% | 0.01% | 0.00% |
| EB | 0.01% | 0.01% | 0.00% | 0.01% |
| Cumene | 95.89% | 88.92% | 57.51% | 49.63% |
| DIPB | 2.55% | 7.22% | 25.81% | 27.81% |
| COMDIPB | 0.00% | 0.01% | 0.03% | 0.07% |
| C8–C10 Aromatics | 0.03% | 0.03% | 0.17% | 0.81% |
| TIPB | 0.01% | 0.08% | 1.38% | 2.02% |
| C10+ | 0.36% | 0.39% | 0.86% | 2.21% |
| Cumene Conversion | 4.11% | 11.08% | 42.49% | 50.37% |
| Selectivities | | | | |
| MDIPB | 59.04% | 61.22% | 64.79% | 65.03% |
| ODIPB | 1.77% | 1.01% | 0.62% | 0.67% |
| PDIPB | 39.18% | 37.77% | 34.59% | 34.30% |
| MDIPB:ODIPB Ratio | 33.3 | 60.6 | 103.9 | 97.4 |

It will be seen from Table 7 that at cumene conversions of 40–50%, USY gave a mixture of DIPB isomers in which the meta:ortho ratio was in excess of 95 and the by-product yield was low.

EXAMPLE 8

Disproportionation of Cumene Over US-Y

The process of Example 2 was repeated but with the catalyst being 2 g of RE-Y (crushed 1/8" extrudates with 35% alumina binder) diluted with about 2 g of sand. The results are shown in Table 8.

TABLE 8

| Conditions | | |
|---|---|---|
| Temperature, C. | 160 | 180 |
| Pressure, psig | 850 | 850 |
| WHSV | 2 | 2 |
| Reactor Effluent | | |
| C5– | 0.00% | 0.01% |
| Benzene | 2.34% | 4.56% |
| Toluene | 0.00% | 0.01% |
| EB | 0.01% | 0.00% |
| Cumene | 92.72% | 84.38% |
| DIPB | 4.48% | 10.05% |
| COMDIPB | 0.00% | 0.01% |
| C8–C10 Aromatics | 0.03% | 0.04% |
| TIPB | 0.02% | 0.18% |
| C10+ | 0.41% | 0.75% |
| Cumene Conversion | 7.28% | 15.61% |
| Selectivities | | |
| MDIPB | 61.14% | 62.63% |
| ODIPB | 1.19% | 0.87% |
| PDIPB | 37.67% | 36.50% |
| MDIPB:ODIPB Ratio | 51.4 | 72.4 |

Although significantly less active than USY, it will be seen from Table 8 that RE-Y was effective to disproportionate cumene into a mixture of DIPB isomers in which the meta:ortho ratio exceeded 50.

EXAMPLE 9

Disproportionation of Cumene Over MCM-68

The process of Example 1 was repeated but with the catalyst being 2 g of MCM-68 (crushed 1/8" extrudates with 35% alumina binder) diluted with about 2 g of sand. The results are shown in Table 9.

TABLE 9

| Conditions | | | | | | |
|---|---|---|---|---|---|---|
| Temperature, C. | 170 | 180 | 190 | 200 | 210 | 220 |
| Pressure, psig | 850 | 850 | 850 | 850 | 850 | 850 |
| WHSV | 2 | 2 | 2 | 2 | 2 | 2 |
| Reactor Effluent (wt %) | | | | | | |
| C5– | 0.04% | 0.09% | 0.22% | 0.00% | 0.00% | 0.05% |
| C6–C7 Hydrocarbons | 0.00% | 0.00% | 0.00% | 0.00% | 0.00% | 0.00% |
| Benzene | 0.00% | 0.08% | 0.22% | 0.67% | 1.42% | 4.13% |
| Toluene | 0.02% | 0.00% | 0.00% | 0.02% | 0.02% | 0.10% |
| EB | 0.00% | 0.00% | 0.00% | 0.00% | 0.00% | 0.01% |
| Cumene | 99.61% | 99.47% | 98.82% | 97.52% | 95.20% | 86.48% |
| DIPB | 0.06% | 0.09% | 0.42% | 1.32% | 2.96% | 8.69% |
| COMDIPB | 0.00% | 0.00% | 0.00% | 0.00% | 0.00% | 0.00% |
| C8–C10 Aromatics | 0.07% | 0.03% | 0.05% | 0.06% | 0.05% | 0.11% |
| TIPB | 0.00% | 0.00% | 0.00% | 0.00% | 0.00% | 0.01% |
| C10+ Aromatics | 0.20% | 0.25% | 0.27% | 0.39% | 0.34% | 0.43% |
| Cumene Conversion | 0.39% | 0.53% | 1.18% | 2.48% | 4.80% | 13.52% |
| Selectivities | | | | | | |
| MDIPB | 48.15% | 48.20% | 48.74% | 48.83% | 48.86% | 57.39% |
| ODIPB | 1.50% | 1.40% | 0.31% | 0.13% | 0.06% | 0.05% |
| PDIPB | 50.34% | 50.39% | 50.95% | 51.04% | 51.08% | 42.55% |
| MDIPB:ODIPB Ratio | 32.0 | 34.3 | 156.5 | 377.9 | 779.0 | 1047.1 |

EXAMPLE 10

COMPARATIVE

Disproportionation of Cumene Over ZSM-12

The procedure of Example 2 was repeated but with the catalyst being 2 g of ZSM-12 (crushed 1/16" extrudates with 35% alumina binder) diluted with about 2 g of sand. Cumene was introduced to the reactor at 2 WHSV over a range of temperatures (100 to 240° C.), but under all the conditions tested the catalyst was inactive for cumene disproportionation. ZSM-12 is a molecular sieve having pores defined by non-intersecting 12-membered ring channels having cross-sectional dimensions of 5.5 Angstrom by 5.9 Angstrom.

EXAMPLE 11

COMPARATIVE

Disproportionation of Cumene Over ZSM-5

The procedure of Example 2 was repeated but with the catalyst being 2 g of ZSM-5 (crushed 1/16" extrudates with 35% alumina binder) diluted with about 2 g of sand. Cumene was introduced to the reactor at 2 WHSV over a range of temperatures (100 to 240° C.), but under all the conditions tested the catalyst was inactive for cumene disproportionation. ZSM-5 is a molecular sieve having pores defined by two sets of intersecting 10-membered ring channels, one set of channels having cross-sectional dimensions of 5.3 Angstrom by 5.6 Angstrom and the other set having cross-sectional dimensions of 5.1 Angstrom by 5.5 Angstrom.

We claim:

1. A process for the selective production of meta-diisopropylbenzene and para-diisopropylbenzene, said process comprising the step of contacting a feed containing cumene under disproportionation conditions with a catalyst comprising a molecular sieve having pores with a minimum cross-sectional dimension of at least 6 Angstrom to produce a disproportionation effluent containing benzene and a mixture of diisopropylbenzene isomers, said mixture of diisopropylbenzene isomers having a ratio of meta to ortho-diisopropylbenzene greater than 100, wherein the feed is substantially free of benzene and is free of added sulfide; and wherein part of the diisopropylbenzene in the disproportionation effluent is recycled to the contacting step.

2. The process of claim 1, wherein said molecular sieve has pores with cross-sectional dimensions of between 6 and 7 Angstrom.

3. The process of claim 1, wherein said molecular sieve is selected from the group consisting of mordenite, zeolite beta, zeolite Y and MCM-68.

4. The process of claim 1 wherein said molecular sieve is mordenite.

5. The process of claim 4, wherein said molecular sieve is TEA-mordenite having an average crystal size less than 0.5 micron.

6. The process of claim 1, wherein said disproportionation conditions include a temperature of about 100 to about 300° C., a pressure of about 20 to about 5000 psig, a WHSV of about 0.01 to about 100 and a hydrogen to hydrocarbon molar ratio of 0 (no hydrogen added) to about 50.

7. The process of claim 1, wherein said disproportionation conditions include a temperature of about 140 to about 220° C., a pressure of about 20 to about 500 psig, a WHSV of about 0.01 to about 10 and a hydrogen to hydrocarbon molar ratio of about 0 to about 5.

8. The process of claim 1, and comprising the initial steps of alkylating benzene with propylene to produce an alkylation effluent comprising cumene and then using at least part of said alkylation effluent as the feed to said contacting step.

9. The process of claim 8, wherein at least part of the benzene produced by said contacting step is recycled to the alkylating step.

10. The process of claim 1, wherein said effluent, prior to any separation step, contains less than 1 wt % of n-propylbenzene, less than 5 wt % of triisopropylbenzenes, and less than 5 wt % of reaction products other than benzene and diisopropylbenzenes; and said effluent, prior to any separation step, contains less than 1% of ortho-diisopropylbenzene by weight of the total diisopropylbenzene content of said effluent.

* * * * *